(12) United States Patent
Shah et al.

(10) Patent No.: US 8,158,061 B2
(45) Date of Patent: Apr. 17, 2012

(54) AUTOMATED SLIDE STAINING APPARATUS

(75) Inventors: Preyas Shah, Warminster, PA (US); Leonard C. Wagner, Coopersburg, PA (US)

(73) Assignee: Rushabh Instruments, LLC, Warrington, PA (US)

( * ) Notice: Subject to any disclaimer, the term of this patent is extended or adjusted under 35 U.S.C. 154(b) by 617 days.

(21) Appl. No.: 12/331,838

(22) Filed: Dec. 10, 2008

(65) Prior Publication Data
US 2010/0144018 A1    Jun. 10, 2010

(51) Int. Cl.
*G01N 21/00* (2006.01)
(52) U.S. Cl. ........... 422/65; 422/63; 422/64; 422/66; 422/67; 436/43; 436/46; 436/47; 436/48; 436/50
(58) Field of Classification Search ............. 422/63–67; 436/43, 46–48, 50
See application file for complete search history.

(56) References Cited

U.S. PATENT DOCUMENTS

| | | |
|---|---|---|
| 3,356,096 A | 12/1967 | Davis et al. |
| 3,507,292 A | 4/1970 | Pederson |
| 3,837,795 A | 9/1974 | Becker et al. |
| 3,903,908 A | 9/1975 | Logue et al. |
| 4,034,700 A | 7/1977 | Bassett et al. |
| 4,092,952 A | 6/1978 | Wilkie et al. |
| 4,651,671 A | 3/1987 | Pedersen |
| 4,911,098 A | 3/1990 | Tabata |
| 5,009,185 A | 4/1991 | Stokes et al. |
| 5,180,606 A | 1/1993 | Stokes et al. |
| 5,700,346 A | 12/1997 | Edwards |
| 5,839,091 A | 11/1998 | Rhett et al. |
| 6,076,583 A | 6/2000 | Edwards |
| 6,096,271 A | 8/2000 | Bogen et al. |
| 6,180,061 B1 | 1/2001 | Bogen et al. |
| 6,183,693 B1 | 2/2001 | Bogen et al. |
| 6,349,264 B1 | 2/2002 | Rhett et al. |
| 6,387,326 B1 | 5/2002 | Edwards et al. |
| 6,541,261 B1 | 4/2003 | Bogen et al. |
| 6,585,936 B1 | 7/2003 | Shah |
| 6,635,225 B1 | 10/2003 | Thiem et al. |
| 6,673,620 B1 | 1/2004 | Loeffler et al. |
| 6,735,531 B2 | 5/2004 | Rhett et al. |
| 6,746,720 B2 | 6/2004 | Nishida et al. |
| 6,746,851 B1 | 6/2004 | Tseung et al. |
| 6,783,733 B2 | 8/2004 | Bogen et al. |
| 6,800,249 B2 | 10/2004 | De La Torre-Bueno |
| 6,827,900 B2 | 12/2004 | Thiem et al. |
| 6,998,270 B2 | 2/2006 | Tseung et al. |
| 7,028,831 B2 | 4/2006 | Veiner |
| 7,217,392 B2 | 5/2007 | Bogen et al. |
| 7,226,788 B2 | 6/2007 | De La Torre-Bueno |
| 7,264,111 B2 | 9/2007 | Veiner |
| 7,303,725 B2 | 12/2007 | Reinhardt et al. |
| 7,875,242 B2 * | 1/2011 | Shah .................... 422/65 |
| 2005/0282292 A1 * | 12/2005 | De La Torre-Bueno ...... 436/180 |
| 2006/0188405 A1 * | 8/2006 | Shah ...................... 422/100 |

* cited by examiner

*Primary Examiner* — Lyle Alexander
(74) *Attorney, Agent, or Firm* — RatnerPrestia

(57) ABSTRACT

A slide stainer assembly is disclosed. The slide stainer includes a slide carrier that is configured to carry one or more laboratory slides and a plurality of slide processing stations for processing the slides. A transport member including a plurality of engagement portions is configured for releasably engaging the slide carrier. A drive mechanism is coupled to the transport member. The drive mechanism is configured to move the transport member in a cyclical path such that, in the course of one cycle, the transport member engages a slide carrier docked in a first station, removes the slide carrier from the first station, docks the slide carrier in a second station and returns to the first station to engage another slide carrier.

14 Claims, 16 Drawing Sheets

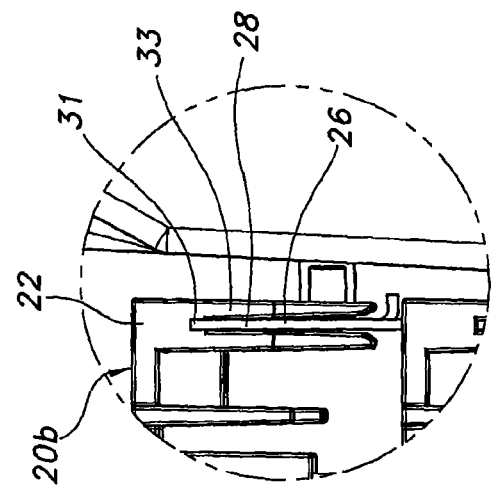
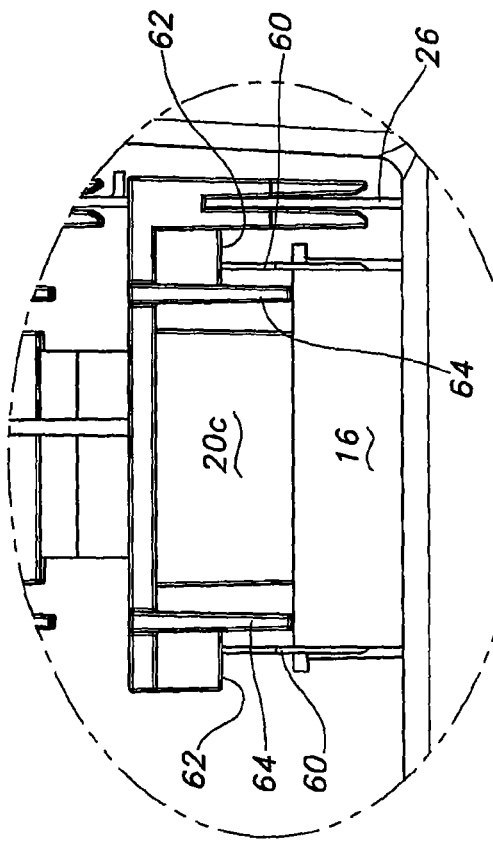
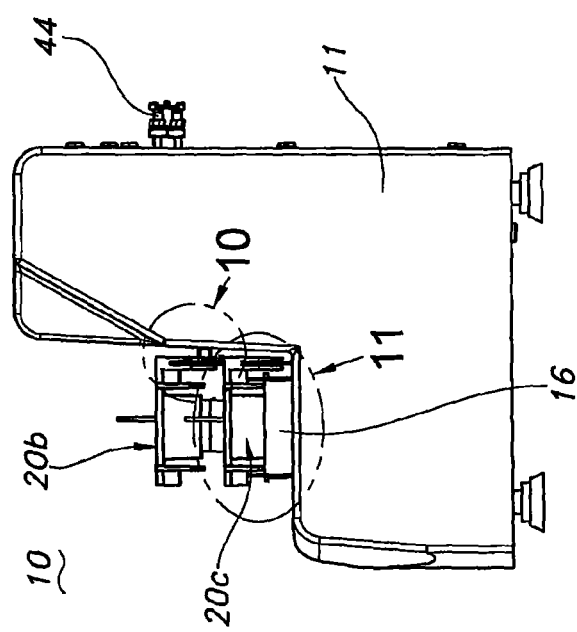

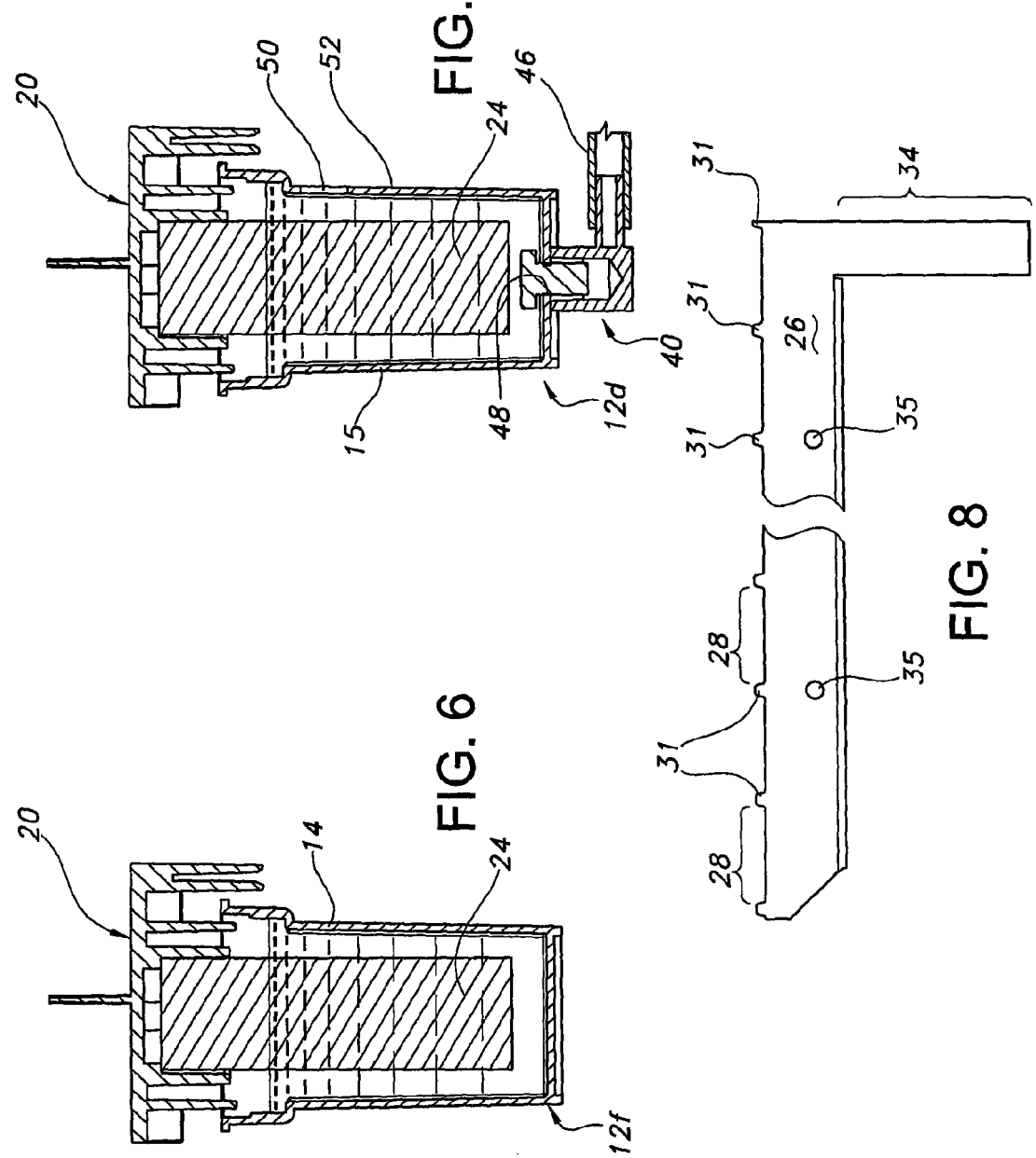

AUTOMATED SLIDE STAINING APPARATUS

FIELD OF THE INVENTION

The present invention relates to an apparatus for staining laboratory slides.

BACKGROUND OF THE INVENTION

Laboratories routinely stain biological tissue specimens deposited on laboratory slides for subsequent pathologic examination to detect and/or monitor tissue abnormalities. Automated tissue staining systems allow batch staining of large numbers of slides containing tissue specimens for subsequent examination. In the course of a staining process, the tissue specimens are exposed to a series of well-defined processing steps that ultimately produces a properly stained specimen for examination. Automation of the staining process significantly reduces the time required to stain tissue specimens, reduces the incidence of human error and allows processing parameters to be altered in an efficient manner. Improvements to slide staining systems are continually sought in the interest of reliability, performance, speed and cost.

SUMMARY OF THE INVENTION

According to one aspect of the invention, a slide stainer assembly is disclosed. The slide stainer includes a slide carrier that is configured to carry one or more laboratory slides. A plurality of slide staining and/or slide rinsing stations are provided on the slide stainer. Each station is configured to process the slides of the slide carrier. The slide stainer includes a transport member including a plurality of engagement portions. Each engagement portion is configured for releasably engaging a slide carrier. A drive mechanism is coupled to the transport member. The drive mechanism is configured to move the transport member in a cyclical path such that, in the course of one cycle, the transport member engages a slide carrier docked in a first station, removes the slide carrier from the first station, docks the slide carrier in a second station disengages the first slide and returns to the first station to engage another slide carrier.

According to another aspect of the invention, the slide stainer includes a storage vessel positioned adjacent the second station. The storage vessel is sized for receiving a plurality of slide carriers each including one or more processed laboratory slides. The drive mechanism is configured to move the transport member in a cyclical path such that, in the course of one cycle, (i) the engagement portion of the transport member engages and removes a first slide carrier from the second station, (ii) the extended segment of the transport member translates a second slide carrier that is positioned within the storage vessel to accommodate the first slide carrier, and (iii) positions the first slide carrier in the storage vessel.

BRIEF DESCRIPTION OF THE DRAWINGS

The invention is best understood from the following detailed description when read in connection with the accompanying drawing. It is emphasized that, according to common practice, the various features of the drawing are shown schematically and may not be to scale. Included in the drawing are the following figures:

FIG. 4 depicts a right-side elevation view of the slide stainer of FIG. 1.

FIG. 6 depicts a cross-sectional view of a staining station taken along the lines 6-6 of FIG. 3, wherein a slide carrier assembly is shown docked in the staining station (docked slide carrier assembly not shown in FIG. 3).

FIG. 7 depicts a cross-sectional view of a rinsing station taken along the lines 7-7 of FIG. 3, wherein a slide carrier assembly is shown docked in the rinsing station (docked slide carrier assembly not shown in FIG. 3).

FIG. 8 depicts a front elevation view of a portion of the transport member of FIG. 1.

FIG. 10 depicts a detailed view of the slide stainer of FIG. 4 illustrating the engagement between the transport member and a slide carrier assembly.

FIG. 11 depicts a detailed view of the slide stainer of FIG. 4 illustrating the engagement between a processed slide carrier assembly and the storage vessel.

DETAILED DESCRIPTION OF THE INVENTION

Figure 1:
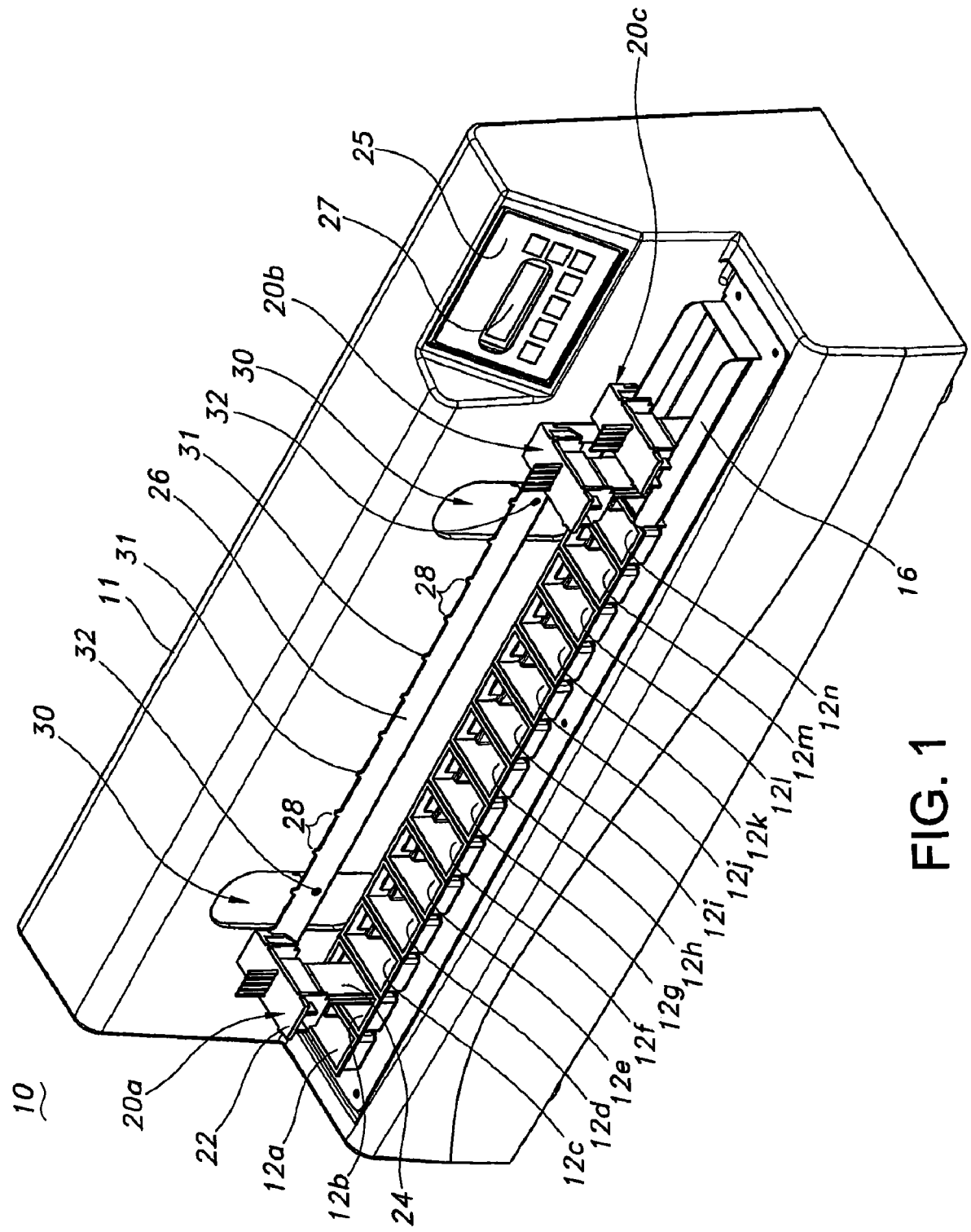
FIG. 1 depicts a perspective view from the top, right corner of a slide stainer according to one exemplary embodiment of the invention.
Figure 2:
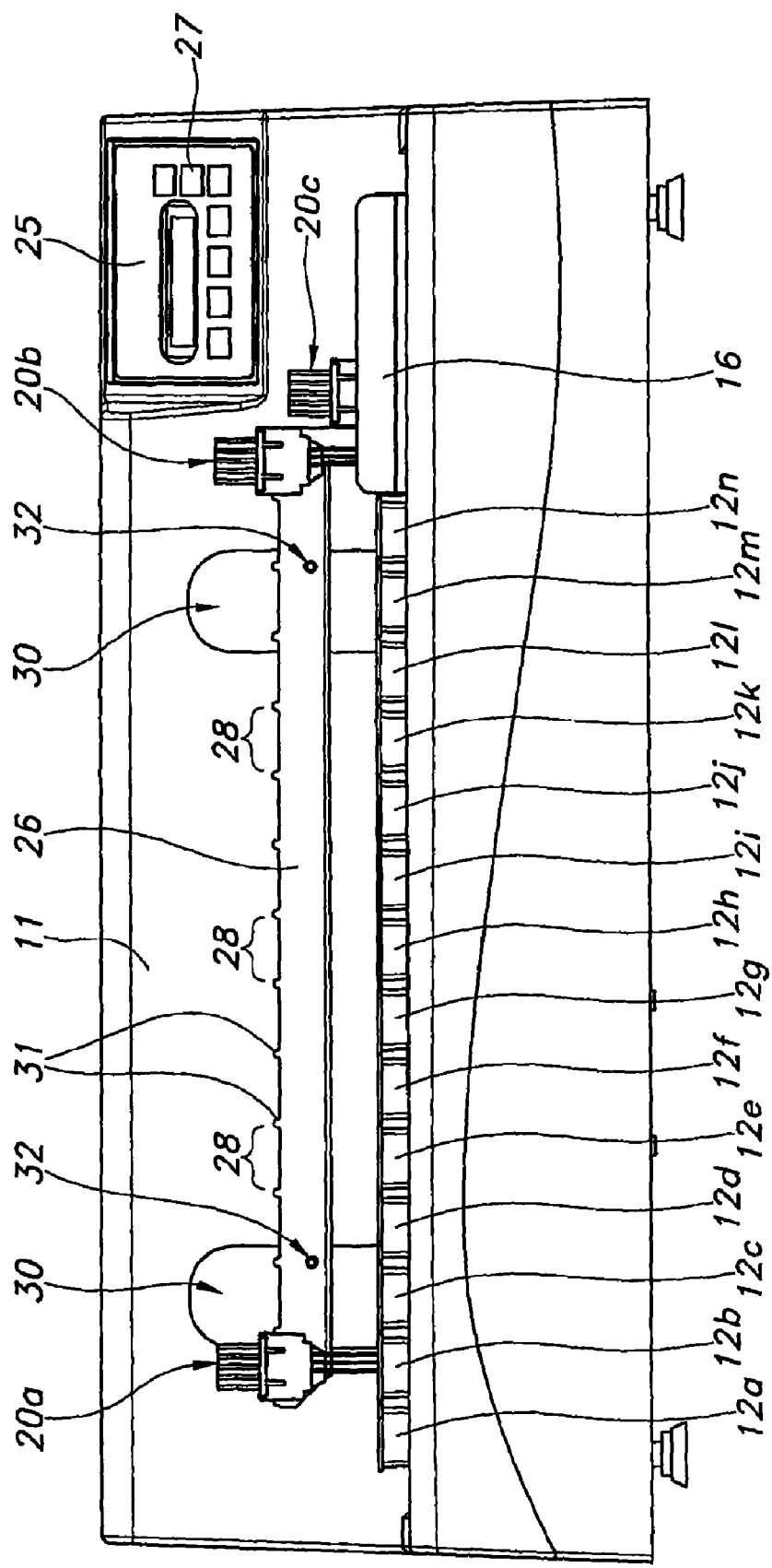
FIG. 2 depicts a front elevation view of the slide stainer of FIG. 1.

The invention will next be illustrated with reference to the figures. Such figures are intended to be illustrative rather than limiting and are included herewith to facilitate explanation of the present invention. In the figures, like item numbers refer to like elements throughout. When a plurality of similar elements are present, a single reference numeral may be assigned to the plurality of similar elements with a small letter designation referring to specific elements. When referring to the elements collectively or to a non-specific element, the small letter designation may be omitted.

FIGS. 1-5 depicts perspective, front elevation, top plan, right side elevation and partially exploded views, respectively, of slide stainer 10 according to one exemplary embodiment of the invention. Slide stainer 10 includes a plurality of slide processing stations 12a-12n for staining, rinsing, or otherwise processing, laboratory slides. Illustrated housing 11 of slide stainer 10 includes a substantially rectangular recess 13 (see FIG. 5) that is sized to accommodate stations 12a-12n and storage vessel 16. Storage vessel 16 is positioned adjacent the right-most station 12n in the illustrated embodiment for storing one or more processed slides after laboratory slides are sequentially processed in stations 12a through 12n.

Each slide processing station 12 (hereinafter station 12) in the illustrated embodiment includes a vessel that may be filled with either a reagent for staining the slide, or a rinsing medium, such as water, for rinsing the slide. In alternative embodiments, one or more of the stations may be a drying station or other type of station that would be understood by one of skill in the art from the description herein. In the embodiment shown in FIGS. 1-5, station 12d is a rinsing station and stations 12a-12c and 12e-12n are staining stations. It should be understood that any station may be a staining station, a rinsing station or other type of station and slide stainer 10 is not limited to the particular configuration shown. Moreover, the vessels associated with stations 12a-12n may be removable from housing 11 of slide stainer 10, such that stations 12 within slide stainer 10 may be reconfigured to the operator's requirements.

Slide stainer 10 is configured to sequentially transport one or more slide carrier assemblies 20 to each station 12a-12n and then to storage vessel 16 under the control of an electronics control unit (ECU) 25 (described below), for example. Each station 12a-12n is configured to receive a single slide carrier assembly 20. Each slide carrier assembly 20 includes slide carrier 22 and a plurality of laboratory slides 24 releasably mounted to slide carrier 22. A laboratory specimen (not shown) is mounted to each laboratory slide 24. Further details of slide carrier assembly 20 are described with reference to FIGS. 16-18. Three (3) slide carrier assemblies 20a, 20b and 20c are illustrated in the exemplary embodiment depicted in the figures. It will be understood by those skilled in the art from the description herein that slide stainer 10 may interface with multiple slide carrier assemblies 20.

Illustrated storage vessel 16 can accommodate four (4) processed slide carrier assemblies 20. Those skilled in the art will recognize that storage vessel 16 may be configured to accommodate any number of slide carrier assemblies 20. The ECU 25 may be configured to maintain an active count of the number of processed slide carrier assemblies 20 within the storage vessel 16. In operation, once three (3) processed slide carrier assemblies 20 are contained within storage vessel 16, ECU 25 may issue a distinctive audible warning (such as three beeps) alerting the operator to the near-filled condition. After the fourth processed slide carrier assembly 20 is inserted into storage vessel 16, storage vessel 16 is completely filled with processed slide carrier assemblies. Accordingly, once the fourth processed slide carrier assembly 20 is inserted into storage vessel 16, ECU 25 may deactivate slide stainer 10 to prevent further processed slide carrier assemblies from being placed into the filled storage vessel 16. Alternatively, a sensor (not shown) may be provided in storage vessel 16 to sense when it is completely filled with processed slide carrier assemblies 20. Such a sensor may send a signal to ECU 25 of slide stainer 10 to either warn the operator or deactivate slide stainer 10.

Figure 3:
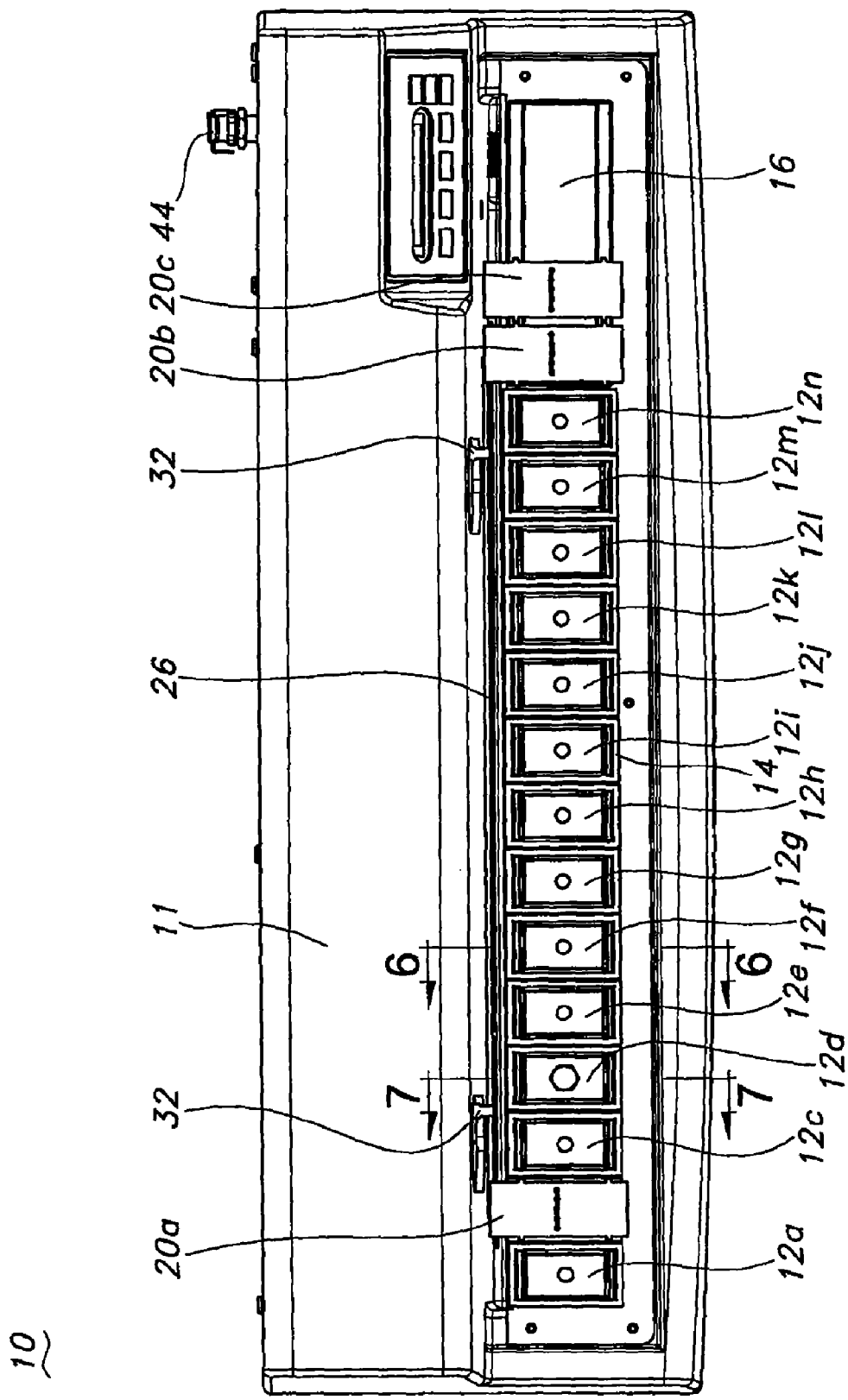
FIG. 3 depicts a top plan view of the slide stainer of FIG. 1.
Figure 5:
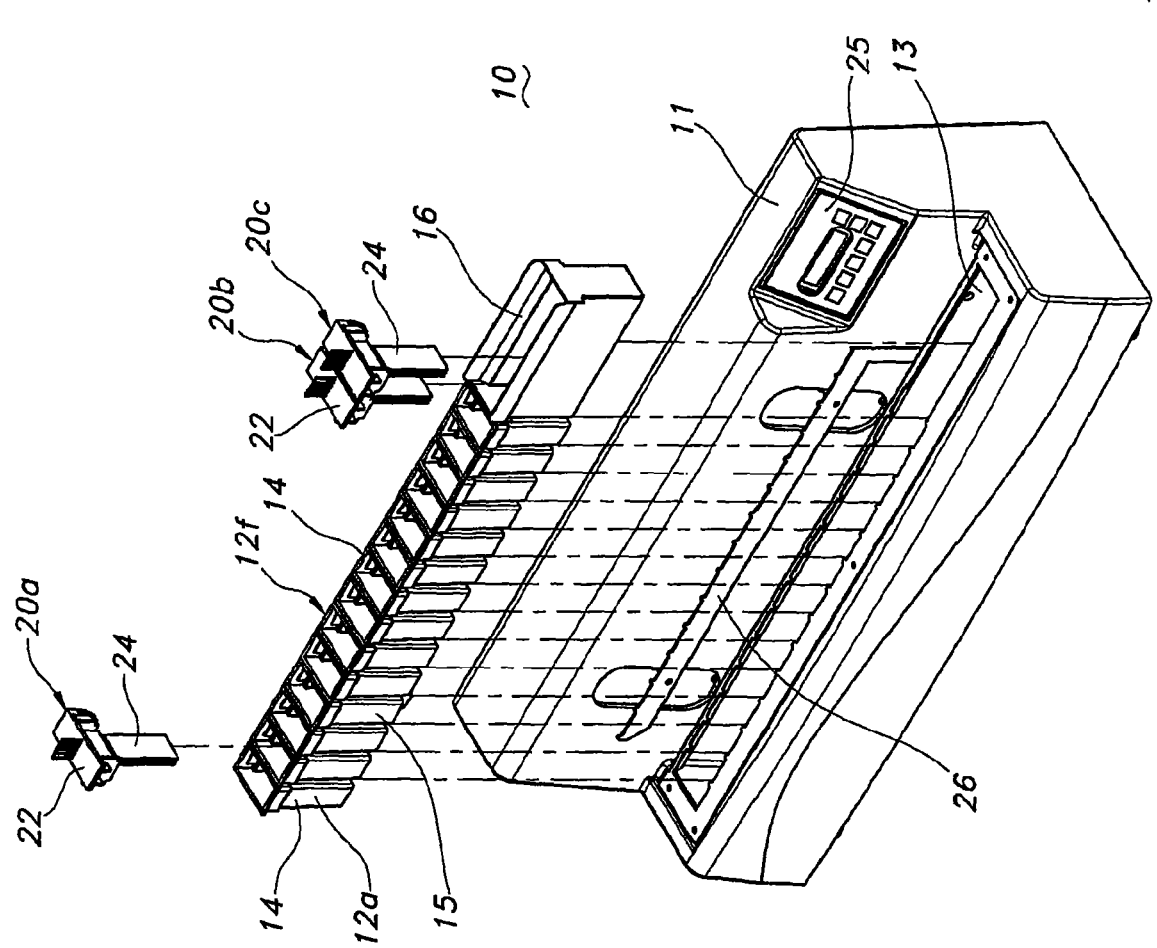
FIG. 5 depicts a partially-exploded view of the slide stainer of FIG. 1.

FIG. 6 depicts a cross-sectional view of staining station 12f taken along the lines 6-6 of FIG. 3. Slide carrier assembly 20 is shown docked in staining station 12f (not shown in FIG. 3). Staining station 12f generally includes vessel 14 that is filled with a reagent for staining laboratory slides 24 of slide carrier assembly 20. Vessel 14 may be sized to contain about 50 milliliters of fluid, for example. Slides 24 of slide carrier assembly 20 are submerged in the reagent bath.

FIG. 7 depicts a cross-sectional view of rinsing station 12d taken along the lines 7-7 of FIG. 3. Slide carrier assembly 20 is shown docked in rinsing station 12d (not shown in FIG. 3). Rinsing station 12d generally includes vessel 15 filled with liquid (e.g., water) for rinsing laboratory slides 24 of slide carrier assembly 20. Slides 24 of slide carrier assembly 20 are at least partially submerged in the water bath. Water (or other rinsing fluid) is delivered into vessel 15 through fluid dispersion device 40 that is mounted to the bottom end of vessel 15. Fluid dispersion device 40 is fluidly coupled to inlet port 44 (see FIG. 4) of slide stainer 10 by a fluid supply line 46. Inlet port 44 is coupled to a water source. Although not shown, a valve is coupled to inlet port 44 for selectively controlling the flow of fluid through fluid supply line 46.

Fluid dispersion device 40 disperses the flow of rinse fluid entering vessel 15 such that, during rinsing, the flow of rinse fluid is not concentrated in any particular area within vessel 15. By dispersing the flow of rinse fluid, all laboratory slides 24 within vessel 15 are subject to substantially the same rinse fluid flow. Further details of fluid dispersion devices are disclosed in U.S. Pat. No. 6,585,936 to Shah, which is incorporated by reference herein in its entirety.

Vessel 15 includes an opening 48 on its bottom surface for receiving fluid dispersion device 40 and an opening 50 on side surface 52 for draining excess rinse fluid from vessel 15. Accordingly, when the fluid level within vessel 15 reaches opening 50, the fluid drains from vessel 15 through opening 50. Although not shown, a drain port is defined in recess 13 of slide stainer housing 11 for transporting the excess rinse fluid away. A universal vessel may be used for staining station 12f and rinsing station 12d. If the same vessel is used in both stations, plugs may be applied over openings 48 and 50 when vessel 15 is used in a staining station.

FIG. 8 depicts a front elevation view of a portion of transport member 26. Transport member 26 is provided for sequentially transporting slide carrier assemblies 20 to adjacent stations 12 and then to storage vessel 16. Transport member 26 is optionally a flat sheet of material. A plurality of engagement portions 28 (14 shown) are defined on the top surface of transport member 26. Each engagement portion 28 is configured for releasably engaging a single slide carrier 22 of slide carrier assembly 20. Protrusions 31 (see FIG. 6B) are formed on the top surface of transport member 26 opposite each engagement portion 28 for retaining slide carrier 22 in position and restricting slide carrier 22 from sliding along the length of transport member 26. Transport member 26 includes extended segment 34 which extends to an elevation below the right-most engagement portion 28. As described in greater detail with reference to FIG. 9C, extended segment 34 is sized and shaped for advancing a processed slide carrier assembly 20 that is positioned within storage vessel 16 to accommodate an additional processed slide carrier assembly 20.

FIGS. 9A-9F depict a schematic side elevation view of transport member 26 advancing slide carrier assemblies 20a-20c through one cycle. In FIGS. 9A-9F only stations 12a-12c, 12m and 12n are shown and only a portion of transport member 26 is shown for simplicity.

Generally, as depicted in FIGS. 9A-9F, transport member 26 sequentially transports slide carrier assemblies 20 to adjacent stations 12 and then to storage vessel 16. Transport member 26 is moved along path 29, as illustrated by broken lines, by a drive mechanism (described below; not explicitly shown in FIGS. 9A-9F) of slide stainer 10. The drive mechanism causes pins 32 to move along their respective paths 29. Pins 32 of the drive mechanism are mounted to transport member 26 through holes 35 provided in transport member 26

(see FIG. 8). Fasteners (not shown) may be utilized to secure transport member 26 to pins 32. In an exemplary embodiment, pins 32 simultaneously move along their respective paths 29, each of the paths 29 have the same trajectory, pins 32 move at the same speed, and, at any time, pins 32 are positioned at the same locations along their respective paths 29. Because pins 32 are fixed to transport member 26, transport member 26 travels along path 29 coincident with pins 32. Those skilled in the art will recognize that the motion of pins 32 may vary from that shown and described without departing from the scope or spirit of the invention.

Figure 9A:
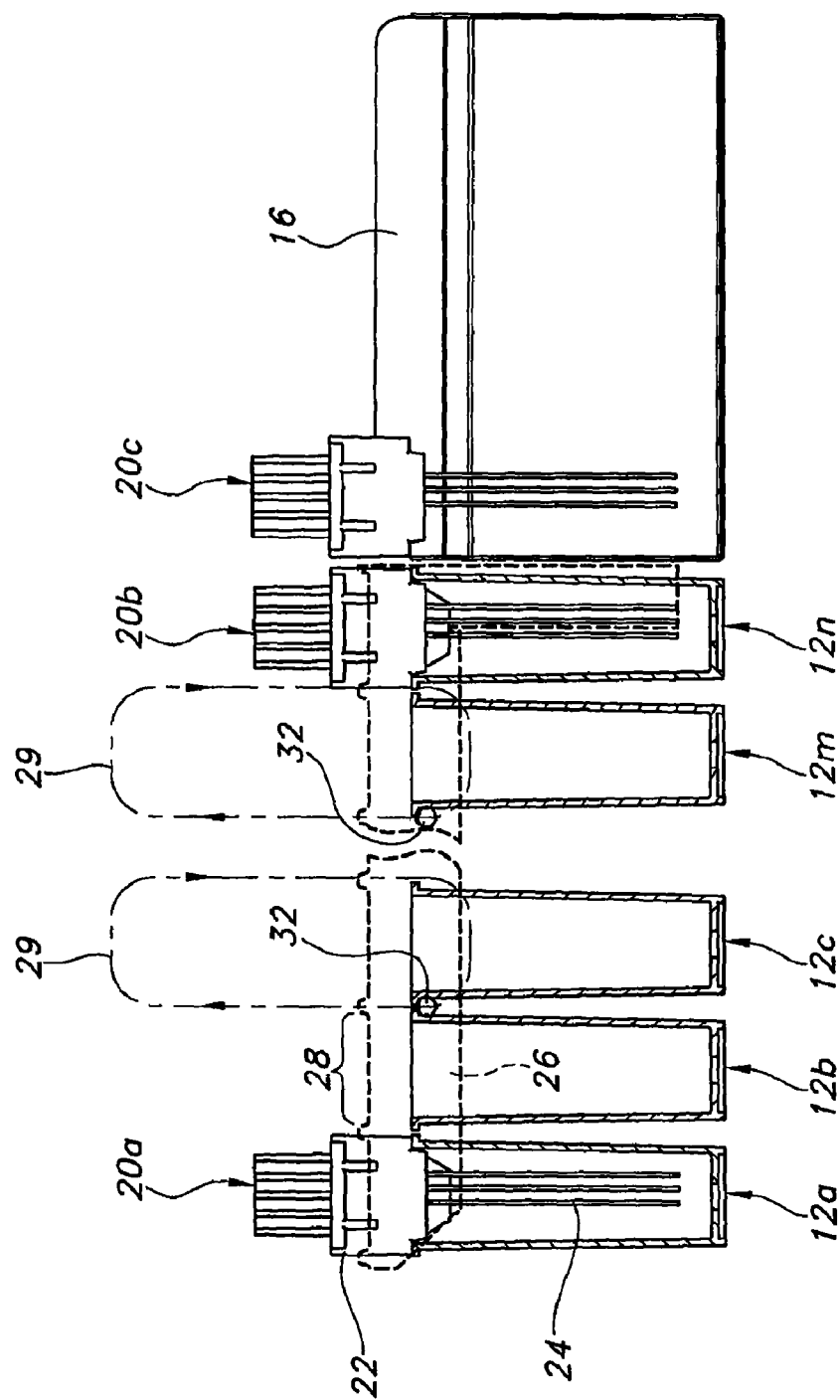
FIGS. 9A-9F depict a schematic front elevation view of the transport member advancing three different slide carrier assemblies through a complete cycle.

FIG. 9A depicts a starting position of slide stainer 10. In the starting position, slide carrier assembly 20a is docked in station 12a, slide carrier assembly 20b is docked in station 12n and slide carrier assembly 20c is docked in storage vessel 16. Slide carriers 22 of slide carrier assemblies 20a and 20b are engaged by engagement portions 28 of transport member 26. Engagement between slide carrier assembly 22b and transport member 26 is shown in FIG. 10.

As shown in FIG. 10, engagement portion 28 of transport member 26 is releasably positioned within recess 33 formed in slide carrier 22 of slide carrier assembly 22b. Protrusions 31 formed on each side of engagement portion 28 retain slide carrier 22 in a fixed position and restrict slide carrier 22 from sliding along the length of transport member 26. Releasable engagement between transport member 26 and slide carrier 22 enables slides 24 to be deposited and removed vertically into and out of vessels 14 and 15.

Those skilled in the art will understand from the description herein that various ways exist to releasably mount a slide carrier to a transport member. For example, a protrusion formed in a slide carrier may be engaged within a recess formed in the transport member. Alternatively, slide carrier may be releasably coupled to the transport member by a pin and slot, a fastener, a plug, a surface or any other device known to those skilled in the art. Accordingly, it may be referred to herein that slide carrier 10 includes means for releasably coupling a slide carrier to the transport member.

Referring back to the configuration shown in FIG. 9A, laboratory slides 24 of slide carrier assemblies 20a and 20b are being processed, i.e., rinsed or stained, for example, whereas slide carrier assembly 20c is not being processed. Once processing of laboratory slides 24 of slide carrier assemblies 20a and 20b is complete, slide stainer 10 is configured to do the following: (1) transport slide carrier assembly 20a to the next station, i.e., station 12b, and (2) transport slide carrier assembly 20b from station 12n to storage vessel 16. It should be understood that station 12n is the final processing station of slide stainer 10 and once processing of the laboratory slides of a slide carrier assembly is complete, the processed slide carrier assembly is ready for temporary storage in storage vessel 16.

Figure 9B:
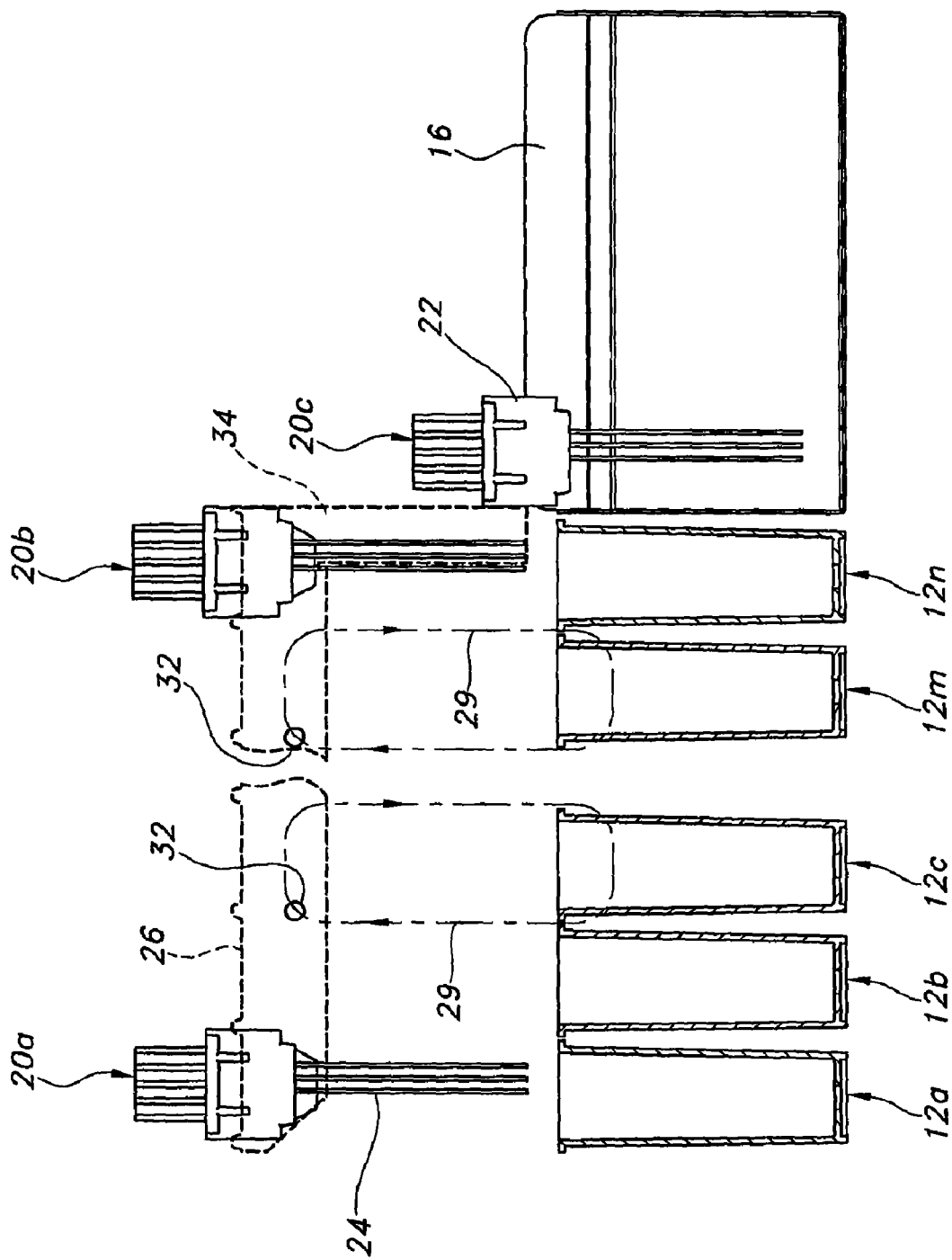

Referring now to FIGS. 9A and 9B, the drive mechanism translates pins 32 in the upward direction along their respective paths 29, as depicted by the arrows on paths 29, from their location shown in FIG. 9A to their location shown in FIG. 9B. Translation of pins 32 causes translation of transport member 26 and slide carrier assemblies 20a and 20b. As noted previously, transport member 26 is fixed to pins 32 and slide carrier assemblies 20a and 20b are releasably engaged with transport member 26, thus, movement of pins 32 causes movement of slide carrier assemblies 20a and 20b. By moving in the upward direction, transport member 26 removes laboratory slides 24 of slide carrier assemblies 20a and 20b from stations 12a and 12n, respectively. As shown in FIG. 9B, extended segment 34 of transport member 26 is positioned to bear against slide carrier 22 of slide carrier assembly 20c.

Figure 9C:
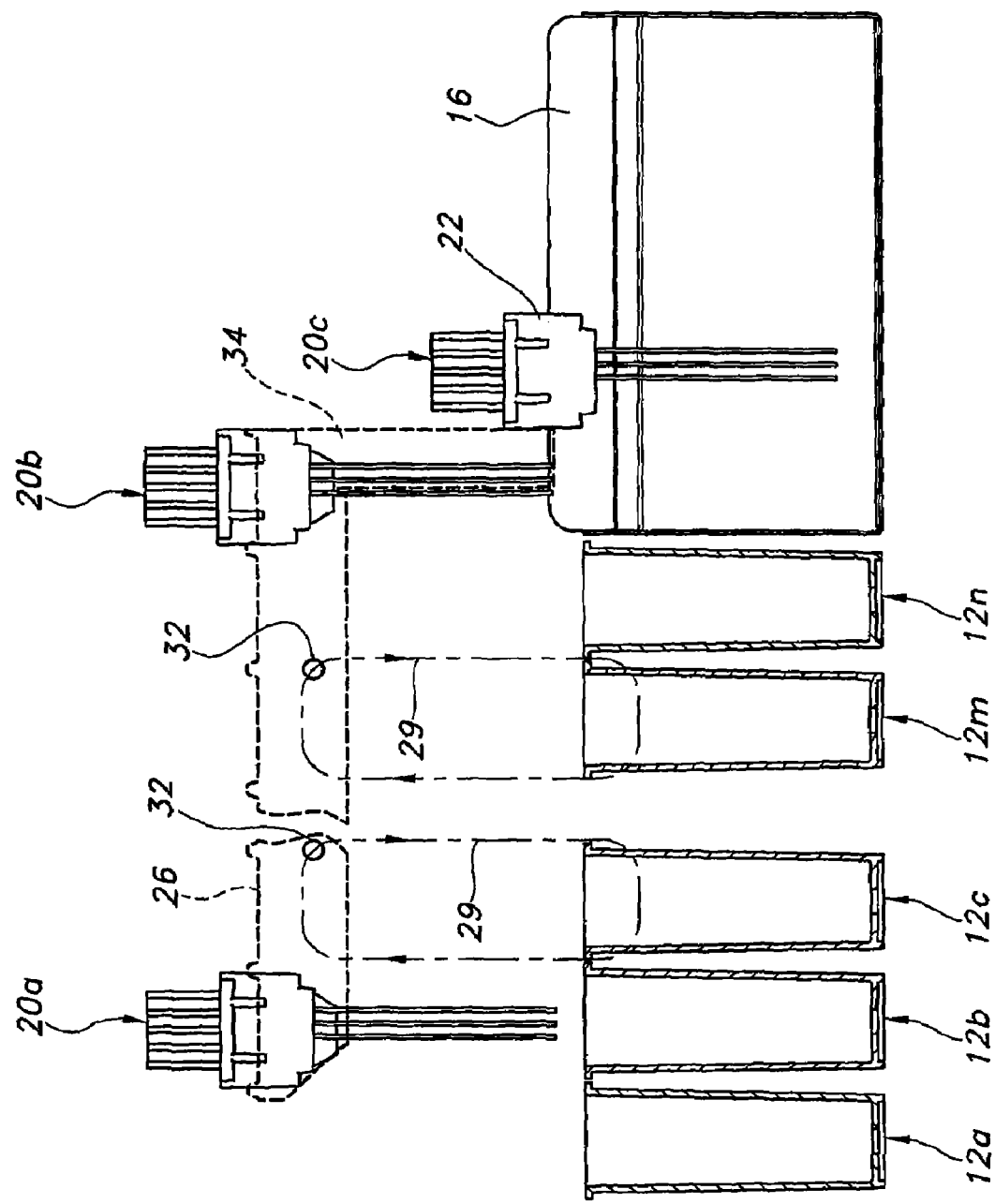

Referring now to FIGS. 9B and 9C, the drive mechanism translates transport member 26 and slide carrier assemblies 20a and 20b in a horizontal direction (to the right) from their location shown in FIG. 9B to their location shown in FIG. 9C. Translating transport member 26 in a horizontal direction by a pre-determined distance causes extended segment 34 of transport member 26 to push slide carrier 22 of slide carrier assembly 20c in a horizontal direction by the same distance. Translating slide carrier assembly 20c within storage vessel 16 provides sufficient room to accommodate slide carrier assembly 20b within storage vessel 16.

Figure 9D:
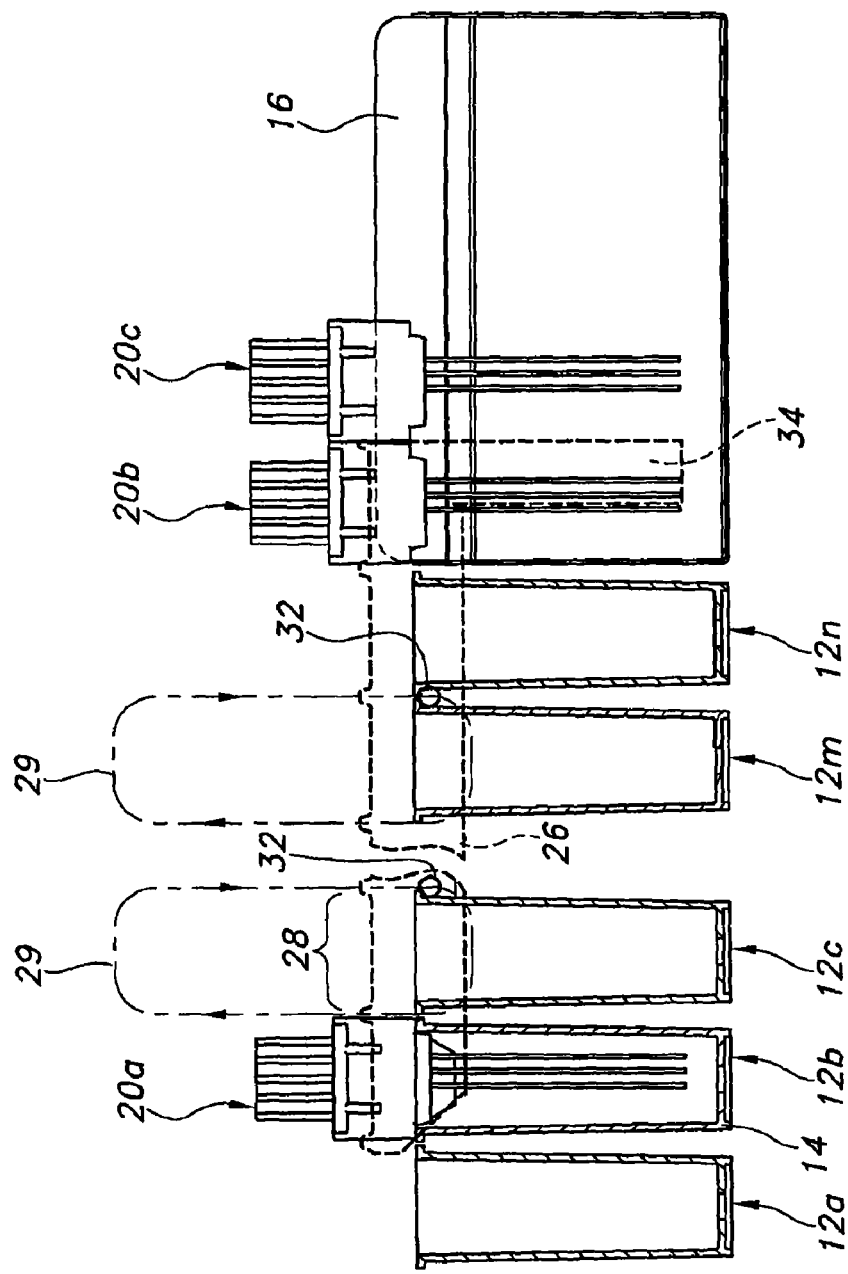

Referring now to FIGS. 9C and 9D, the drive mechanism translates transport member 26 and slide carrier assemblies 20a and 20b in a downward vertical direction from their location shown in FIG. 9C to their docked location shown in FIG. 9D. In FIG. 9D, slide carrier assembly 20a is shown docked in station 12b for processing (e.g., staining or rinsing). Slide carrier assembly 20a remains in the position shown in FIG. 9D for a time-span of between 2 seconds and 300 seconds, for example, to allow processing of the laboratory slides that are immersed in reagent-filled station 12b.

In a docked position the underside surface of carrier 20 of slide carrier assembly 20a (or any slide carrier assembly for that matter) is positioned to bear on the top lip of vessel 14. In FIG. 9D, slide carrier assembly 20b is shown docked in storage vessel 16 beside slide carrier assembly 20c. Engagement between slide carrier assembly 20c and storage vessel 16 is illustrated in FIG. 11. As shown in FIG. 11, walls 60 extending from opposite sides of storage vessel 16 rest on underside surfaces 62 of slide carrier 22 of slide carrier assembly 20c.

Figure 9E:
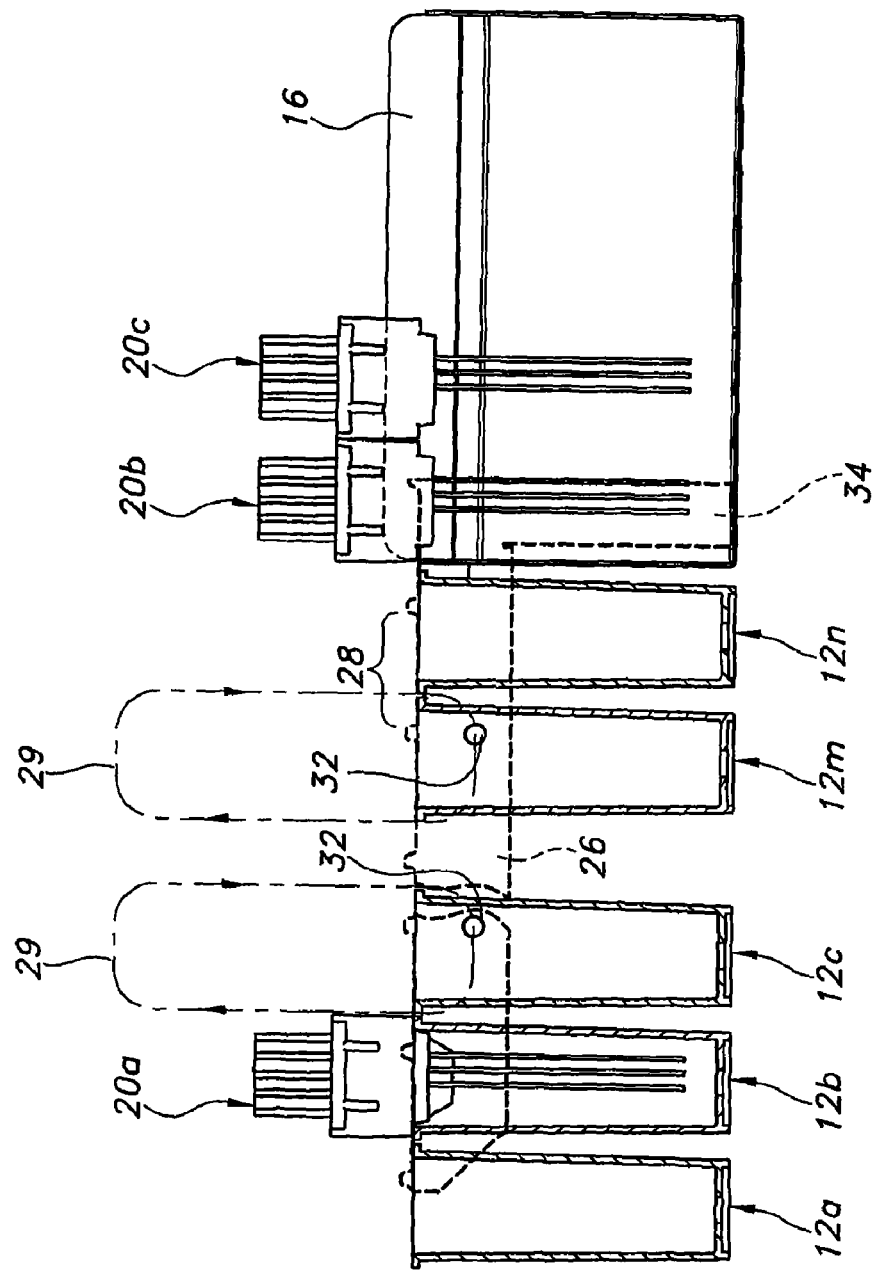

Referring now to FIGS. 9D and 9E, in the motion of transport member 26 from its position shown in FIG. 9D to its position shown in FIG. 9E, transport member 26 disengages from slide carrier assemblies 20a and 20b. Specifically, in FIG. 9D engagement portions 28 of transport member 26 are engaged with slide carrier assemblies 20a and 20b. The drive mechanism translates transport member 26 downward (and to the left) from its location shown in FIG. 9D to its location shown in FIG. 9E. In its downward movement, engagement portions 28 of transport member 26 release from slide carrier assemblies 20a and 20b. In other words, in FIG. 9E transport member 26 is completely detached from slide carrier assemblies 20a and 20b.

Figure 9F:
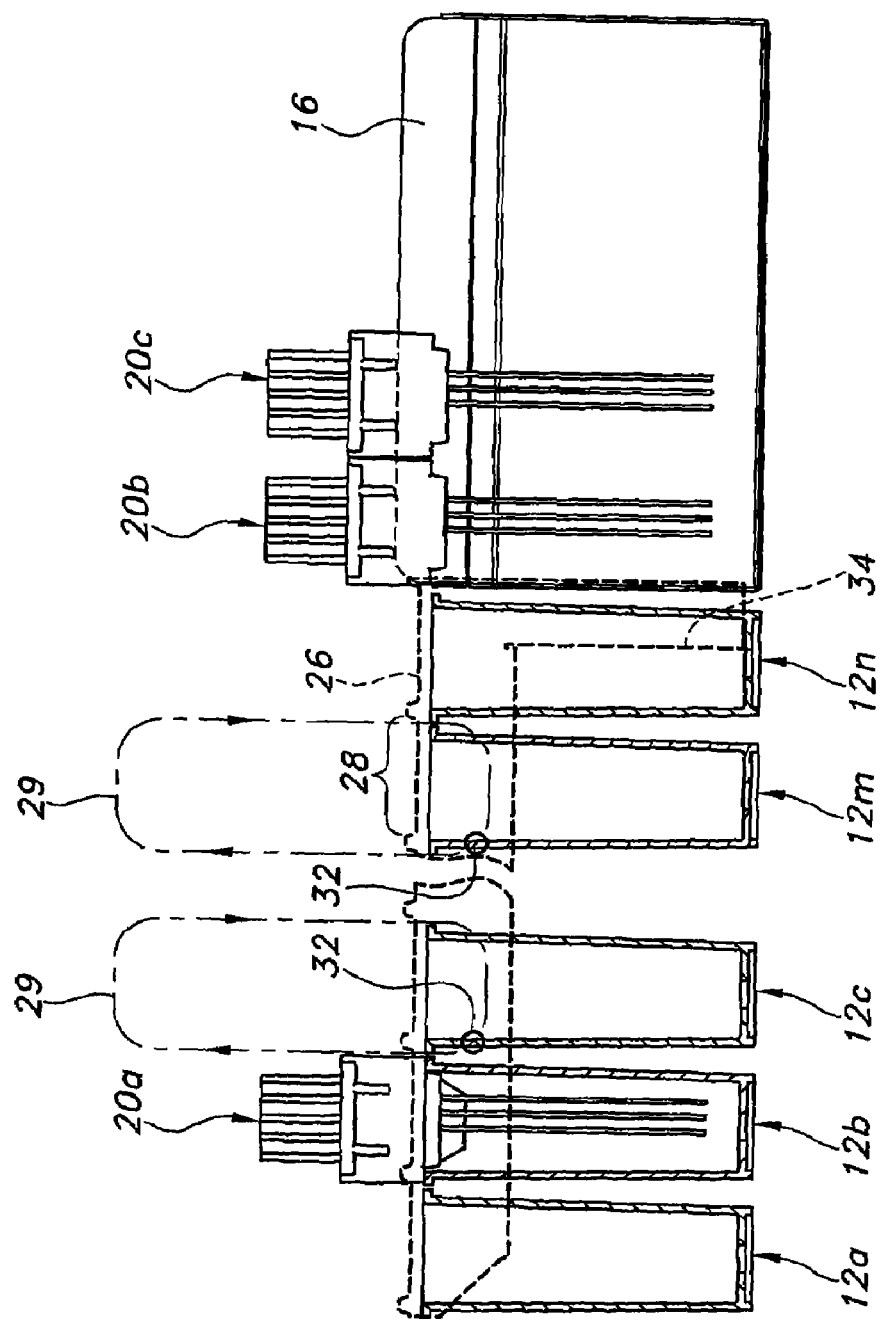

Referring now to FIGS. 9E and 9F, the drive mechanism translates transport member 26 further to the left and in an upward direction from its location shown in FIG. 9E to its location shown in FIG. 9F. In its upward movement, engagement portion 28 of transport member 26 engages slide carrier assembly 20a. Transport member 26 is positioned in the same location in FIG. 9F as it is shown in FIG. 9A. Although not shown, it should be understood that in the next cycle of transport member 26, slide carrier assembly 20a is moved to station 12c and slide carrier assemblies 20b and 20c are slid to the right within vessel 16 to accommodate another processed slide carrier assembly (not shown).

Referring generally to FIGS. 9A-9F, transport member 26 of slide stainer 10 performs the following steps in the course of one cycle: (1) engages a first slide carrier assembly in a first station (either a staining station or a rinsing station); (2) removes the first slide carrier assembly from the first station; (3) moves a second processed slide carrier assembly that is positioned within the storage vessel 16 to accommodate another processed slide carrier assembly; (4) positions the first slide carrier assembly in a second station (either a staining station, a rinsing station or the storage vessel) that is adjacent the first station; and (5) returns to the first station to engage another slide carrier assembly.

In FIGS. 9A-9F only three slide carrier assemblies 20 are shown. According to this exemplary embodiment, up to fourteen (14) slide carrier assemblies 20 may be coupled to transport member 26 at any time. Additionally, it should be understood that if transport member 26 includes more than fourteen (14) engagement portions 28 then transport member 26 can accommodate more than fourteen (14) slide carrier assemblies 20. To transfer a single slide carrier assembly 20 sequentially between station 12a and storage vessel 16, drive mechanism would move transport member 26 through fourteen (14) complete cycles.

Figure 12:
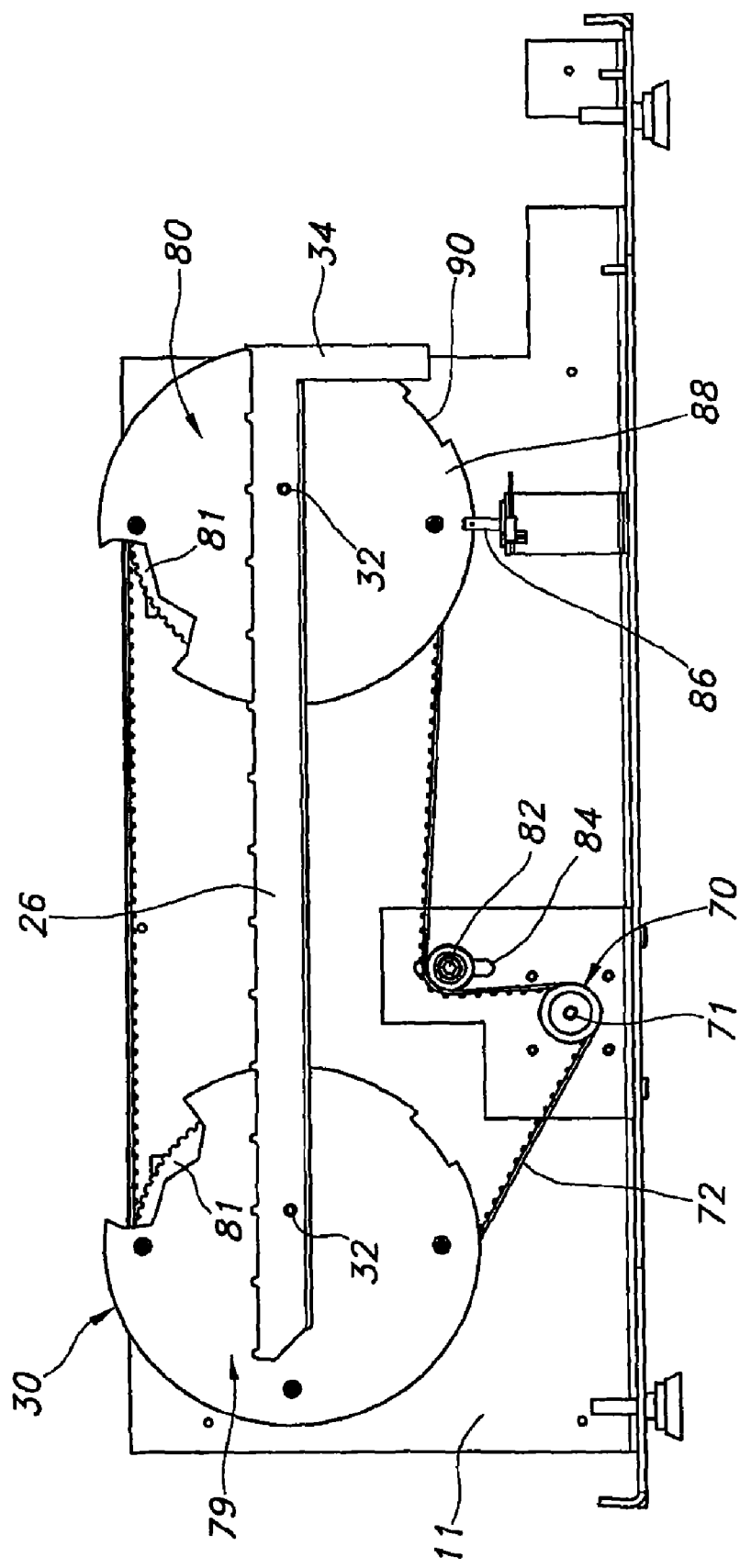
FIG. 12 depicts a front elevation view of the slide stainer of FIG. 1, wherein a portion of the slide stainer housing and the stations are omitted to reveal the drive mechanism of the slide stainer.

FIG. 12 depicts drive mechanism 30 of slide stainer 10. According to one exemplary embodiment, drive mechanism 30 includes motor 70 that is fixed to housing 11. Motor 70 includes a rotating gear shaft 71 having gear teeth for driving toothed belt 72. Toothed belt 72 drives two guiding devices 79 and 80. Each guiding device 79, 80 is shown partially cut-away to reveal the engagement between toothed belt 72 and toothed gear 81 of each guiding device 79 and 80. As explained in greater detail with reference to FIGS. 13-15, guiding devices 79 and 80 are configured to drive transport member 26 along path 29 depicted in FIGS. 9A-9F. The flat side of toothed belt 72 engages roller 82. A slot 84 is provided on housing 11 for adjusting the position of roller 82 to adjust the tension applied to toothed belt 72.

Optical sensor 86 is mounted to housing 11 for activating or deactivating motor 70 based upon the rotational position of guiding device 80. Optical sensor 86 includes a light source that is positioned on one side of cover 88 of guiding device 80 and a light sensor that is positioned on the opposite side of cover 88. The outer edge of cover 88 is positioned between the light source and the light sensor of optical sensor 86 such that the light sensor does not ordinarily detect the light source. As cover 88 rotates about its axis, however, recess 90 formed on the outer edge of cover 88 exposes the light sensor to the light source of optical sensor 86. At the moment recess 90 passes between the light sensor and the light source of optical sensor 86, slide carrier assemblies 20 are docked in their respective stations 12.

Once the light sensor is exposed to the light source of optical sensor 86, optical sensor 86 transmits a signal to ECU 25 (described below) to deactivate motor 70. While slide carrier assemblies 20 are docked in their respective stations 12, the staining and/or rinsing operations commence. After the predetermined amount of time has expired, ECU 25 re-activates motor 70 until recess 90 again exposes the light sensor to the light source of optical sensor 86. Sensor 86 is not limited to that shown and described. Sensor 86 may also be a switch, a Hall-Effect sensor, or any other sensor known to those skilled in the art without departing from the scope of the invention.

Figure 14:
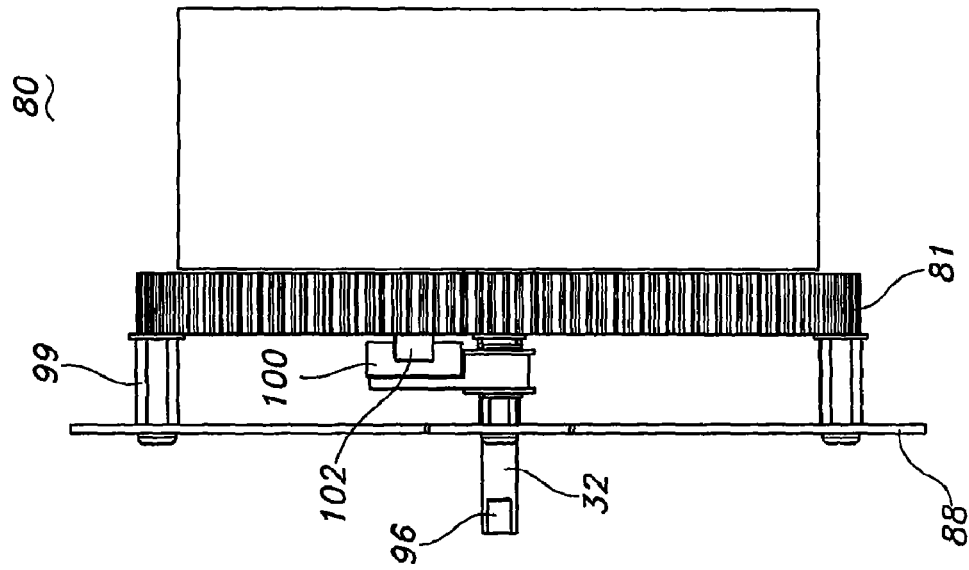
FIG. 14 depicts a right side elevation view of the guiding device of FIG. 13, wherein a standoff is omitted to reveal a sliding member of the guiding device.
Figure 13:
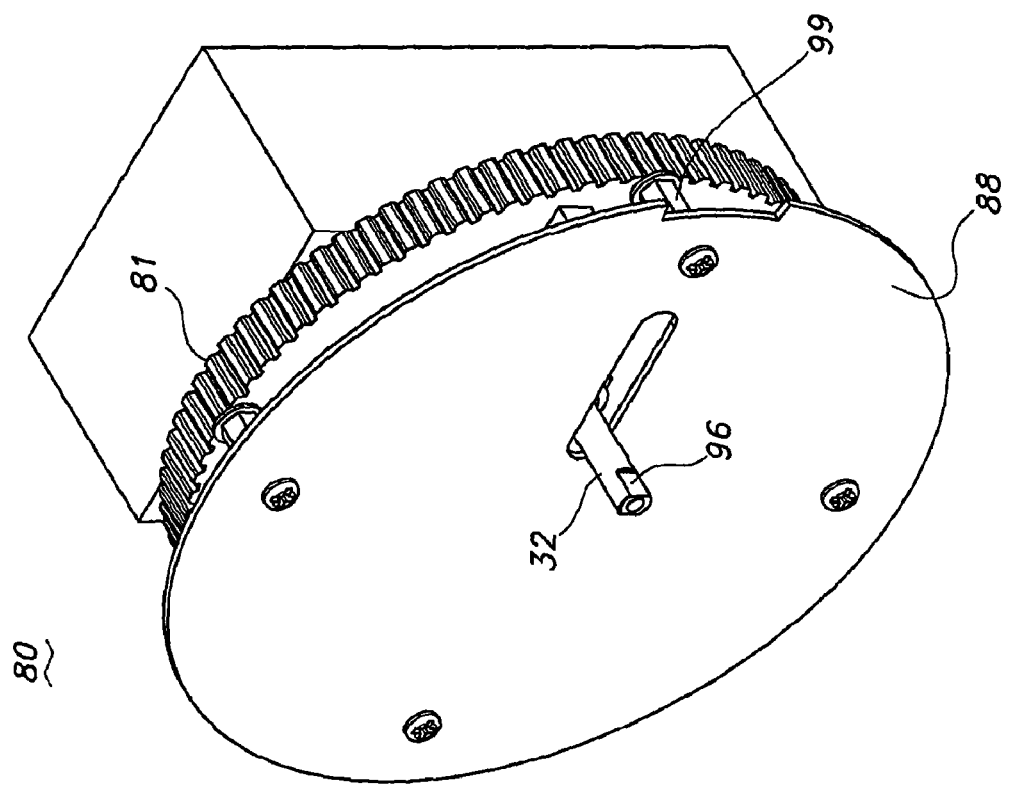
FIG. 13 depicts a perspective view from the top right corner of the guiding device of FIG. 12.
Figure 15:
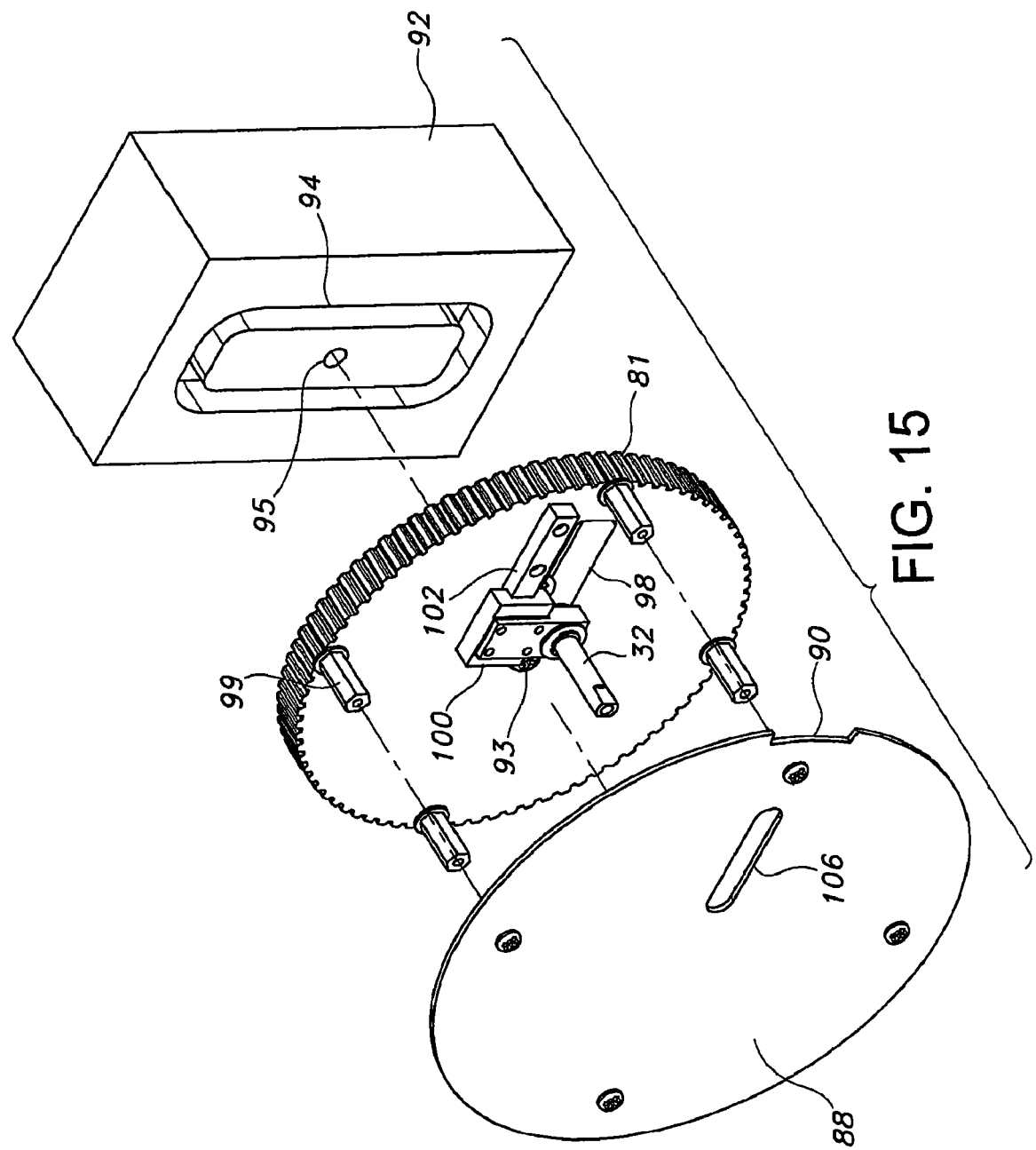
FIG. 15 depicts a partially exploded view of the guiding device of FIG. 13.

FIGS. 13-15 depict perspective, right side elevation and partially exploded views, respectively, of guiding device 80 of FIG. 12. While guiding device 80 is shown and described hereinafter, it should be understood that guiding devices 79 and 80 are structurally and functionally equivalent. Only one guiding device 79 or 80 may be necessary for operation of slide stainer 10. Accordingly, although not shown, slide stainer 10 might only employ a single guiding device 79 or 80.

Guiding device 80 may be considered as a component of drive mechanism 30 because guiding device 80 is configured to guide the motion of transport member 26. Guiding device 80 generally includes plate 92 defining track 94, toothed gear 81 rotatably mounted to plate 92, and cover 88 mounted to toothed gear 81. As described previously, toothed gear 81 is driven (i.e., rotated) by toothed belt 72. Gear 81 is rotatably mounted to plate 92. Plate 92 is either directly or indirectly mounted to housing 11 and is incapable of rotation. Fastener 93 (see FIG. 15) passes through a hole defined in the axis of rotation of gear 81 and mounts through hole 95 defined in plate 92 thereby coupling gear 81 and plate 92 together. Although not shown, a bearing is provided between gear 81 and plate 92 to reduce friction therebetween upon rotation of gear 81.

End 96 of pin 32 is mounted to transport member 26 (see FIGS. 1 and 10) and the opposing end of pin 32 is positioned within track 94 of plate 92. Because pin 32 is positioned within track 94, pin 32 is forced to follow the trajectory of track 94 as gear 81 rotates. The path (i.e. path 29) of pin 32 is illustrated in FIGS. 9A-9F. The trajectory of track 94 may be defined as substantially rectangular, substantially elliptical or defined in the shape of a rectangle having rounded corners.

The body of pin 32 is also positioned within elongated slot 98 (see FIG. 15) that is defined in toothed gear 81. Elongated slot 98 enables pin 32 to follow the trajectory of track 94 as toothed gear 81 rotates about its axis. In the absence of elongated slot 98, pin 32 would bind against a surface of track 94 restricting gear 81 from rotation. As toothed gear 81 rotates about its axis, pin 32 slides along the length of elongated slot 98.

To facilitate sliding action of pin 32, pin 32 is mounted to sliding member 100. Sliding member 100 is slidably mounted to rail 102 which is fixedly mounted to gear 81. Sliding member 100 slides along a surface of rail 102 under the force of gravity and the rotational force of gear 81. Rail 102 is fixedly mounted to gear 81 adjacent elongated slot 98 and extends substantially parallel to elongated slot 98. Those skilled in the art will recognize that rail 102 may be formed directly on a surface of gear 81 and may not be a separate component, as shown. As sliding member 100 slides along a surface of rail 102, pin 32 translates along the length of elongated slot 98.

Cover 88 is mounted to gear 81 by a series of standoffs 99 extending between cover 88 and gear 81. Cover 88 rotates along with year 81. Standoffs 99 separate cover 88 from gear 81 to accommodate sliding member 100 and rail 102. Cover 88 is provided to shield end-user's from the moving components of guiding device 80. Elongated slot 106 is defined in cover 88 to accommodate the sliding action of pin 32. The position, size and shape of elongated slot 106 corresponds to that of elongated slot 98 of gear 81.

Figure 18:
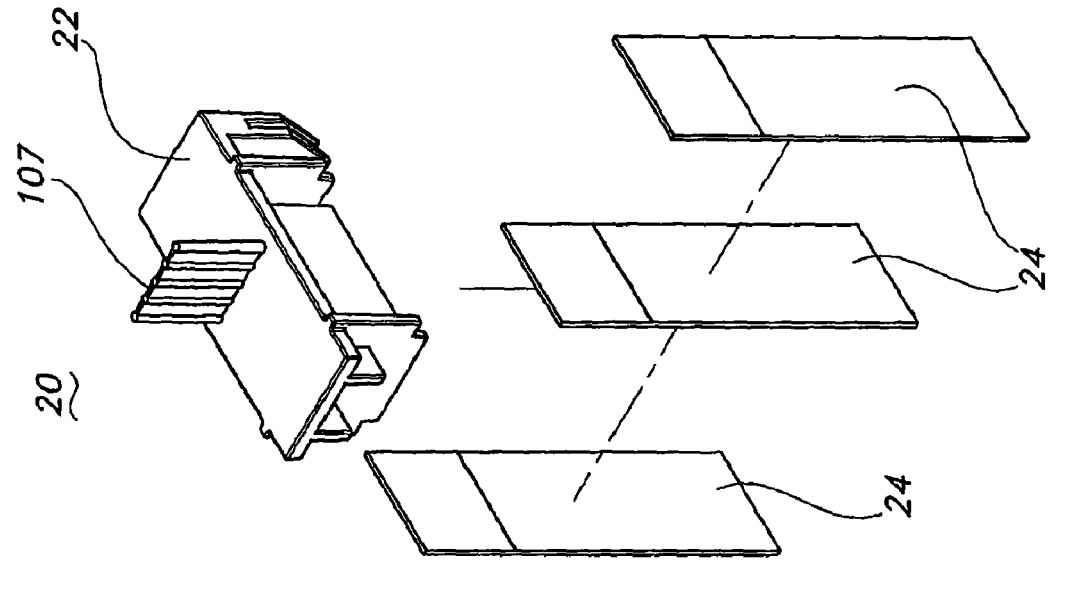
FIG. 18 is an exploded view of the slide carrier assembly of FIG. 16.
Figure 16:
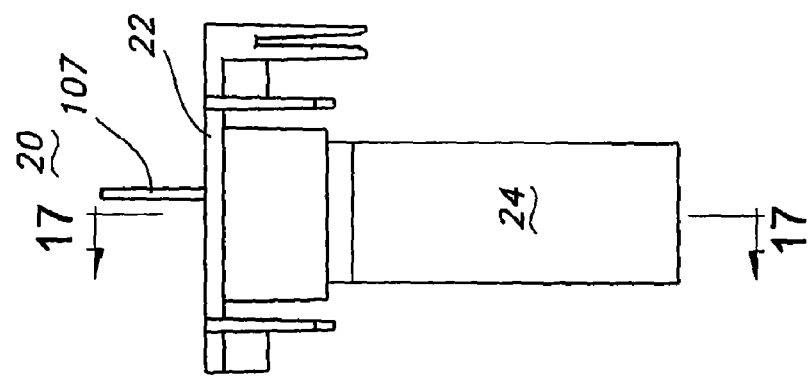
FIG. 16 depicts an elevation view from the right side of a slide carrier assembly.
Figure 17:
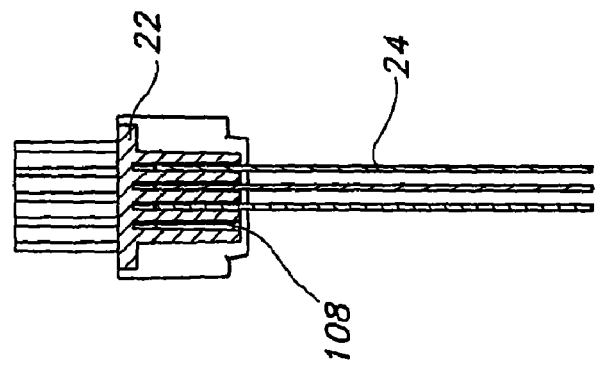
FIG. 17 depicts a cross-sectional view of a slide carrier assembly taken along the lines 17-17 of FIG. 16.

FIG. 16-18 depict elevation, cross-sectional and exploded perspective views of slide carrier assembly 20. Slide carrier assembly 20 includes slide carrier 22 and a plurality of laboratory slides 24 releasably mounted to slide carrier 22. Handle 106 is provided on slide carrier 22 to facilitate handling of slide carrier assembly 20. According to the exemplary embodiment illustrated, three (3) laboratory slides 24 are coupled to slide carrier 22. It will be readily understood by those skilled in the art that any number of laboratory slides 24 may be releasably mounted to slide carrier 22. As best shown in FIG. 17, slide carrier 22 includes a plurality of recesses 108 (four shown). Each recess 108 is sized to releasably captivate a slide. Slides 24 are releasable from slide carrier 22, such that slides 24 may be individually examined by a laboratory technician, stored, or retained individually for further processing. Although not shown, slide carrier 22 may be integrated with a single slide.

Referring now to FIGS. 1 and 12, slide stainer 10 includes electronic control unit (ECU) 25 that is configured to control operation of slide stainer 10. ECU 25 generally includes a programmable processor (not shown) and user interface 27.

ECU 25 receives power from a 12-volt DC power source (not shown) of slide stainer 10. The user interface 27 includes a key pad for entering commands into ECU 25 and a display screen. By way of non-limiting example, the display screen may display the operating status of slide stainer 10, time to completion, warning messages, commands entered via keypad, or any other message. Further details of ECU 25 are described hereinafter with reference to an exemplary operation of slide stainer 10.

In operation of slide stainer 10, an operator first positions a slide carrier assembly into the first station, i.e., station 12a. As described later, the operator may position a slide carrier assembly into any station 12a through 12n at any time. The operator enters a command into the keypad of user interface 27 to start the staining process. ECU 25 activates motor 70 to transport the slide carrier assembly from one station to the next station, as described with reference to FIGS. 9A-9F. Once a slide carrier assembly reaches the next station, ECU 25 is configured to temporarily deactivate motor 70.

Specifically, ECU 25 interfaces with optical sensor 86 (see FIG. 12) to control operation of motor 70. Once the light sensor is exposed to the light source of optical sensor 86, indicating that one staining cycle is complete, optical sensor 86 transmits a signal to ECU 25 to deactivate motor 70. While slide carrier assemblies 20 are docked in their respective stations 12, the staining, rinsing and/or drying operations commence.

To accomplish a rinsing operation, ECU 25 opens a valve (not shown) that is coupled to inlet port 44 to deliver water into rising station 12d at a pre-determined flow rate. The time for staining, rinsing and/or drying the laboratory slides in stations 12a-12n is set by the end-user via the keypad of user interface 27. After the predetermined amount of time has expired, ECU 25 is configured to close the valve coupled to inlet port 44 and reactivate motor 70 until the light sensor is again exposed to the light source of optical sensor 86.

Slide carrier assemblies may be loaded into the first station (or any other station) either before processing has started or after processing has started. A "pause-resume" function of ECU 25 permits the user to pause the transport mechanism after processing has started in order to load additional slide carrier assemblies 20 onto slide stainer 10. The operator enters a command via the keypad of user interface 27 to alert ECU 25 that another slide carrier assembly has been loaded into the first station.

Each time transport member 26 transfers a processed slide carrier assembly 20 to storage vessel 16, ECU 25 issues an audible alert to inform the operator that a processed slide carrier assembly is available for retrieval. If no more slide carrier assemblies 20 are positioned on transport member 26, ECU 25 is configured to deactivate motor 70. The operator physically removes one or more processed slide carrier assemblies and enters a command into the keypad of user interface 27 to inform ECU 25 that one or more processed slide carrier assemblies have been removed from storage vessel 16. ECU 25 then adjusts its count of slide carrier assemblies contained within storage vessel 16 accordingly.

According to the exemplary embodiment, storage vessel 16 is sized to hold four processed slide carrier assemblies 20. In operation, once three (3) processed slide carrier assemblies 20 are contained within storage vessel 16, ECU 25 is configured to issue a distinctive audible warning (such as three beeps) alerting the operator to the near-filled condition. After the fourth processed slide carrier assembly 20 is inserted into storage vessel 16, storage vessel 16 is completely filled with processed slide carrier assemblies. Accordingly, once the fourth processed slide carrier assembly 20 is inserted into storage vessel 16, ECU 25 is configured to deactivate slide stainer 10 to prevent further processed slide carrier assemblies from being placed into the filled storage vessel 16. Alternatively, although not shown, a sensor may be positioned within storage vessel 16 to detect when three or more processed slide carrier assemblies 20 are contained within storage vessel 16. In operation, the sensor would transmit a signal to ECU 25, which would issue a distinctive audible warning (such as three beeps) to alert the operator to the condition and/or deactivate motor 70.

ECU 25 includes a programmable start position feature for staining protocols that do not require the use of all fourteen stations 12a-12n. Using the start position feature, an end-user can specify which station 12a through 12n is being used as the starting position. For example, for a protocol requiring only ten stations, the end-user would place a slide carrier assembly in station 12e. By specifying that station 12e is the starting position, ECU 25 can issue an audible warning once the slides that were originally positioned in station 12e reach storage vessel 16.

ECU 25 of slide stainer 10 is also configured to detect certain motion failures. When a motion error is detected, ECU 25 is configured to perform the following steps: deactivate motor 70, briefly activate motor 70 in a reverse direction, deactivate motor 70 again, re-activate motor 70 in a forward direction in a second attempt to reach the desired position. If after the second attempt ECU 25 detects another motion failure, ECU 25 deactivates motor 70 and issues an audible alert and/or a visual alert on the display screen of user interface 27.

ECU 25 includes other features for adjusting the operation of slide stainer 10 via the keypad of user interface 27. For example, the number of times a slide carrier assembly is immersed in a single station may be adjusted via the keypad of user interface 27. If the operator commands ECU 25 to immerse a slide carrier assembly more than once, ECU 25 would perform the following steps: activate motor 70 in a forward direction to immerse the slides in a station for a first time, deactivate motor 70, activate motor 70 in a reverse direction to remove the slides from that station, deactivate motor 70, re-activate motor 70 in a forward to immerse the slides in that same station for a second time, and so forth. As another example, if the stopping position of transport member 26 is sub-optimal, the position at which transport member 26 stops for processing may be adjusted by the operator via the keypad of user interface 27. Those skilled in the automated slide staining art will recognize other functionalities for ECU 25 from the description herein.

While exemplary embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A slide stainer assembly comprising:
   a slide carrier that is configured to carry one or more laboratory slides;
   at least one slide processing station that is configured to process one or more laboratory slides of the slide carrier;
   a storage vessel positioned adjacent the at least one slide processing station that is sized for receiving a plurality of slide carriers; and
   a transport member including at least one engagement portion configured for releasably engaging the slide carrier and an extended segment spaced from the engagement portion that is at least partially positioned within or adjacent the storage vessel; and a drive mechanism coupled to the transport member, the drive mechanism being configured to move the transport member in a cyclical path such that, in the course of a single cycle, (i) the engagement portion of the transport member engages and removes a first slide carrier from the slide processing station, (ii) the extended segment of the transport member translates a second slide carrier that is positioned within the storage vessel to accommodate the first slide carrier within the storage vessel, (iii) the engagement portion of the transport member positions the first slide carrier in the storage vessel adjacent the second slide carrier, and (iv) the engagement portion of the transport member releases the first slide carrier.

2. The slide stainer assembly of claim 1, wherein the at least one slide processing station is associated with a liquid-holding vessel.

3. The slide stainer assembly of claim 2, wherein the at least one slide processing station is either a rinsing station or a staining station, wherein in a rinsing station configuration the vessel is filled with a rinsing medium and in a staining station configuration the vessel is filled with a reagent.

4. The slide stainer assembly of claim 1, further comprising means for releasably coupling a slide carrier to an engagement portion of the transport member.

5. The slide stainer assembly of claim 4, wherein the coupling means comprises at least one recess formed in the slide carrier that is sized to releasably receive the engagement portion of the transport member.

6. The slide stainer assembly of claim 1, wherein after releasing the first slide carrier, the drive mechanism is further configured to engage a third slide carrier that is positioned in the slide processing station.

7. The slide stainer assembly of claim 1, wherein each slide carrier includes a plurality of slots, each slot being sized to receive a laboratory slide.

8. The slide stainer assembly of claim 1, wherein the drive mechanism comprises:
   a motor;
   a rotatable gear defining an elongated slot, wherein the gear is rotated by the motor;
   a track positioned adjacent the gear and having a defined trajectory; and
   a pin mounted to the transport member and positioned within the track and the elongated slot of the gear such that the pin and the transport member follow the trajectory of the track as the motor rotates the gear.

9. The slide stainer assembly of claim 8, further comprising a sliding member mounted to the gear and positioned adjacent the elongated recess, wherein the pin is mounted to the sliding member such that the sliding member slides along the elongated recess of the gear as the motor rotates the gear.

10. The slide stainer assembly of claim 9, wherein the sliding member slides along or adjacent a surface of the gear under a force of gravity and a rotational force of the gear.

11. The slide stainer assembly of claim 8, wherein the track is a recess or slot that is formed in a plate that is coupled to a housing of the slide stainer and the gear rotates with respect to the plate.

12. The slide stainer assembly of claim 8, wherein the trajectory of the track is substantially rectangular, substantially elliptical or defined in the shape of a rectangle having rounded corners.

13. The slide stainer assembly of claim 8, wherein the slide carrier is configured to slide along a surface of the storage vessel.

14. The slide stainer assembly of claim 1, wherein the extended segment of the transport member translates, but does not lift, the second slide carrier that is positioned within the storage vessel to accommodate the first slide carrier within the storage vessel.

* * * * *